United States Patent [19]

Pontzer

[11] Patent Number: 5,617,850

[45] Date of Patent: Apr. 8, 1997

[54] GAS PROBE

[75] Inventor: Stephen A. Pontzer, Plymouth, Minn.

[73] Assignee: Gold Standard Medical Corp., Leawood, Kans.

[21] Appl. No.: 217,244

[22] Filed: Mar. 24, 1994

[51] Int. Cl.⁶ .................................................. A61B 5/00
[52] U.S. Cl. ............................................ 128/632; 128/635
[58] Field of Search .................................. 128/632, 635

[56] References Cited

U.S. PATENT DOCUMENTS

| | | | |
|---|---|---|---|
| 3,983,864 | 10/1976 | Sielaff et al. | 128/2 |
| 4,016,864 | 4/1977 | Sielaff et al. | 128/2 |
| 4,221,567 | 9/1980 | Clark et al. | 23/230 |
| 4,274,417 | 6/1981 | Delpy | 128/632 |
| 4,516,580 | 5/1985 | Polanyi | 123/632 |
| 4,765,339 | 8/1988 | Jones | 128/632 |
| 4,901,727 | 2/1990 | Goodwin | 128/632 |

FOREIGN PATENT DOCUMENTS

| | | |
|---|---|---|
| 0251027 | 6/1987 | European Pat. Off. |
| 0340908 | 4/1989 | European Pat. Off. |
| 3246728A1 | 7/1983 | Germany . |
| 2053719 | 5/1980 | United Kingdom . |
| WO92/07261 | 4/1992 | WIPO . |

OTHER PUBLICATIONS

Biomedical Business International–Report #1800, 1993, pp. 1–9 through 6–57.

*Primary Examiner*—Angela D. Sykes
*Assistant Examiner*—Stephen Huang
*Attorney, Agent, or Firm*—Westman, Champlin & Kelly, P.A.

[57] ABSTRACT

A blood gas monitoring system monitors blood gas from blood in a blood vessel. A blood probe is introduced into the blood vessel. The blood probe includes a probe body defining a probe chamber and a first gas permeable membrane coupled to a first end of the probe body. A sensor is provided proximate a second end of the probe chamber to sense a desired characteristic of the blood gas. Blood gas is allowed to diffuse across the first gas permeable membrane and into the probe chamber so that the blood gas in the probe chamber is substantially in equilibrium with the blood gas in the blood vessel. Once blood gas in the probe chamber has substantially equilibrated with the blood gas in the blood vessel, the desired characteristic of the blood gas is sensed.

25 Claims, 4 Drawing Sheets

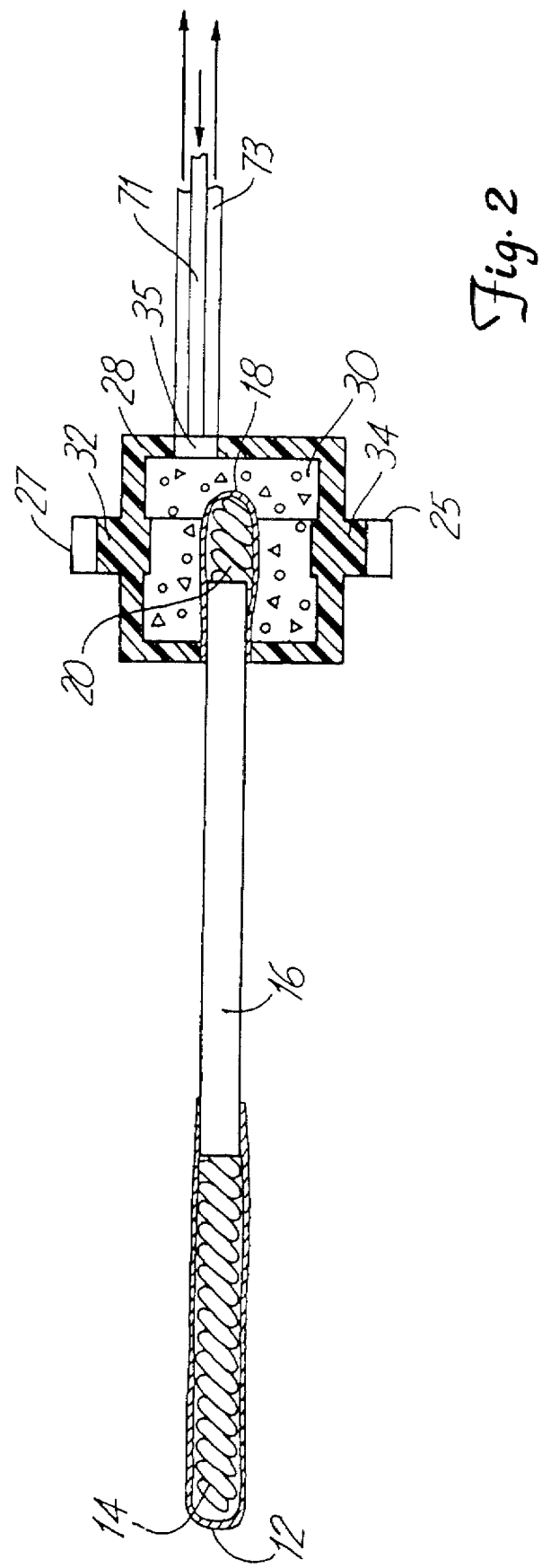

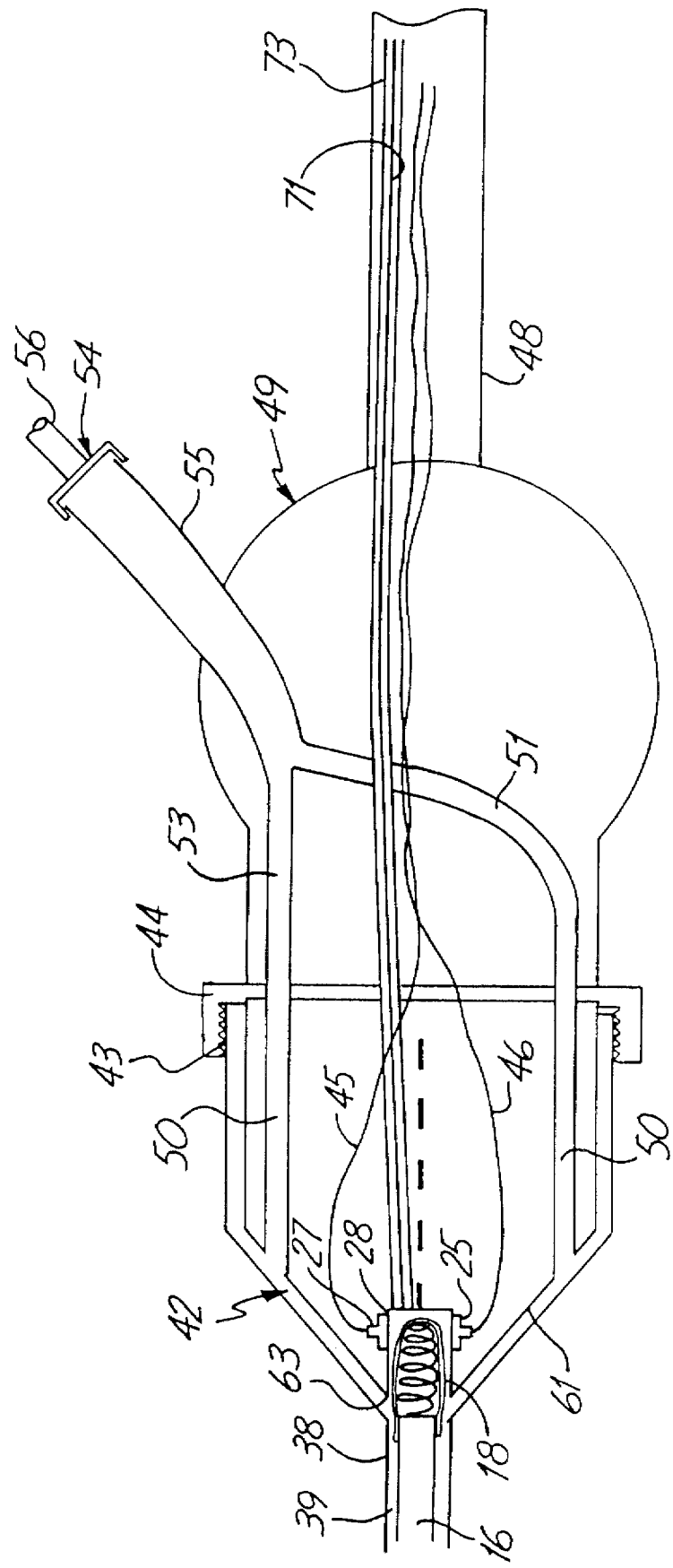

GAS PROBE

BACKGROUND OF THE INVENTION

The present invention relates to blood gas monitoring. More particularly, the present invention relates to a probe used in a system for monitoring blood gases from an artery.

As a person inhales air from the atmosphere, the air enters the alveoli in the lungs. Since the human body utilizes oxygen and expels carbon dioxide, the concentration of oxygen in the air inhaled by a person into the alveoli is higher than the concentration of oxygen in the arterial blood stream. In addition, the concentration of carbon dioxide in the blood stream is higher than the concentration of carbon dioxide in the inhaled air. Thus, according to the law of partial pressure, oxygen diffuses from the lungs, across the alveoli into the bloodstream, and carbon dioxide diffuses from the bloodstream across the alveoli into the lungs. The oxygen is then carried by the bloodstream to the remainder of the body. The carbon dioxide is exhaled from the lungs and therefore expelled by the body.

Due to this interaction, the concentrations of carbon dioxide and oxygen in the blood can give a physician useful diagnostic and treatment information. In short, by measuring arterial blood gases such as oxygen and carbon dioxide, the treating physician can get, among other things, some indication of how well the heart and lungs are operating.

This has given rise to a number of conventional blood gas monitoring techniques. In one conventional blood gas monitoring system, a blood sample is removed from the patient and transported either to a laboratory or to a bed-side analyzer for analysis. The blood sample is analyzed to determine the levels of blood gas in the blood sample drawn from the patient.

A second method is also known for monitoring blood gas. In the second method, a blood gas probe is inserted into the artery. Blood gas is allowed to diffuse across a membrane and is gathered at an in vivo end of the blood gas probe. After a bolus of blood gas has been gathered, the bolus is extracted from the blood gas probe through the use of a vacuum extraction technique. The bolus of blood gas is then monitored in an ex vivo monitor or analyzer.

Both of these conventional techniques have significant disadvantages. First, both techniques rely on taking a sample from the system being analyzed. By definition, such an analyzing or monitoring technique is noncontinuous. Instead, such a technique provides merely a snapshot of the level of blood gas which existed in the system at the time the sample was taken.

Further, depending on where the blood sample or gas sample is analyzed, such techniques can introduce a significant delay. For example, in situations where a blood sample is drawn and analyzed in a lab, it can be 30 to 40 minutes, or even longer, before the physician obtains the results of the analysis. This can introduce a significant delay in providing necessary or desired treatment to the patient.

Also, in systems where a blood sample is drawn from a patient, the blood sample can easily become exposed to the exterior atmosphere. This allows some of the blood gases to diffuse into the gaseous state and other gases to diffuse into the blood sample prior to analysis. Such unwanted diffusion introduces inaccuracies in the results eventually obtained by analysis.

In addition, both techniques involve removing a sample from the system under analysis. The first technique involves removing an actual blood sample, while the second technique involves removing a sample of blood gas. Any time a sample is removed from the system under analysis, the system is altered. Altering the system under analysis introduces further inaccuracies into the results eventually obtained.

Further, in some instances in which arterial blood gas of a patient is being monitored, there has already been significant blood loss (e.g. in neonates) from the patient. In other instances, blood movement through the arterial system is sluggish. Thus, removal of a sample of either blood or blood gas presents the significant dangers of deleteriously depleting the blood or blood gases available for analysis.

Work has also recently been done in attempting to insert the actual blood gas sensors into the artery so they are in contact with the blood to be analyzed. However, such systems have encountered significant problems. First, such sensors are, of necessity, extremely small. Therefore, the sensors only measure blood gas from a very small amount of blood which actually contacts the sensors. In addition, with the sensors actually introduced into the artery, there has been found no effective way of calibrating the sensors. Thus, it is difficult to obtain any meaningful measurement from the sensors.

SUMMARY OF THE INVENTION

The present invention arises from the realization that it is highly desirable to have a blood gas monitoring system which is, for all practical purposes, continuous, and which does not involve removing a sample from the system under analysis. The present invention also arises from the realization that it is desirable to have blood gas sensors external to the artery to allow an efficient mechanism for calibrating the blood gas sensors.

A blood gas monitoring system monitors blood gas from blood in a blood vessel. A blood probe is introduced into the blood vessel. The blood probe includes a probe body defining a probe chamber and a first gas permeable membrane coupled to a first end of the probe body. A sensor is provided proximate a second end of the probe chamber to sense a desired characteristic of the blood gas. Blood gas is allowed to diffuse across the first gas permeable membrane and into the probe chamber so that the blood gas in the probe chamber is substantially in equilibrium with the blood gas in the blood vessel. Once blood gas in the probe chamber has substantially equilibrated with the blood gas in the blood vessel, the desired characteristic of the blood gas is sensed.

BRIEF DESCRIPTION OF THE DRAWINGS

FIG. 2 shows the blood gas probe of FIG. 1 with blood gas sensors arranged about the blood gas probe.

FIG. 3 is a side sectional view of an ex vivo configuration used in conjunction with the blood gas probe of FIG. 1.

DETAILED DESCRIPTION OF THE PREFERRED EMBODIMENTS

Figure 1:
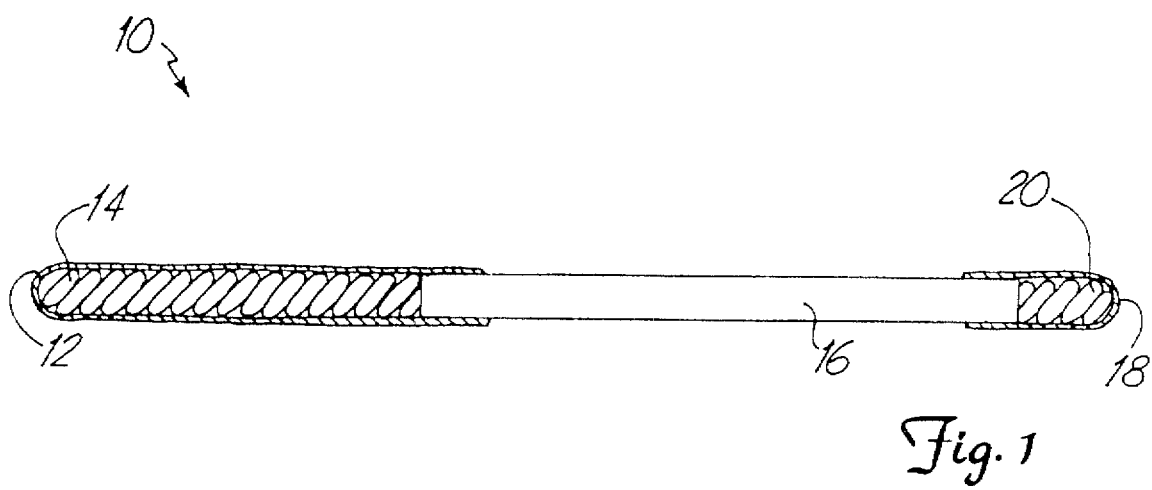
FIG. 1 shows a side sectional view of a blood gas probe according to the present invention.

FIG. 1 is a side sectional view of blood gas probe 10. Probe 10 includes first membrane 12, first support member 14, tube 16, second membrane 18 and second support member 20. In the preferred embodiment, membranes 12 and 18 are gas permeable, liquid impermeable membranes supported by support members 14 and 20, respectively. Tube 16 has a tubule which communicates with the interior chambers defined by membranes 12 and 18.

In use, membrane 12 is inserted into an artery and is in fluid communication with the blood from which gas is to be monitored. The blood gas diffuses across membrane 12 into the interior chamber defined by membrane 12. The blood gas then diffuses down along the tubule (or probe chamber) of tube 16 and into the interior chamber defined by membrane 18. The blood gas then diffuses across membrane 18 where it communicates with blood gas sensors which sense the desired gases.

Once membrane 12 is inserted into the artery, the gases in the interior chamber defined by membrane 12, the tubule of tube 16 and the interior chamber defined by membrane 18 are allowed to equilibrate with the blood gases in the bloodstream. Once in equilibrium, the gases which diffuse across membrane 18 can be measured. This provides a continuous and accurate indication of the concentrations of blood gas in the artery into which membrane 12 is introduced.

In the preferred embodiment, membranes 12 and 18 are both formed of the same material which can be polyester, silicone, Teflon, or any other suitable material. In addition, in one preferred embodiment, membrane 12 has an exterior surface which is formed of a clotting resistant material. Alternatively, membrane 12 may have an exterior surface which has been modified to become a clotting resistant surface. In addition, in the preferred embodiment, tube 16 is formed of polyester, or Teflon, or any other suitable material. Tube 16 should be formed of a suitable material to bond well with membranes 12 and 18. In addition, tube 16 should have sufficient stiffness so that a physician can insert membrane 12 into a desired artery. So long as tube 16 has such stiffness, any suitable material having additional stiffness can be used, depending upon user preference.

Probe 10 should be formed with a minimum length, as this directly affects equilibration time. It has been found that in a system in which tube 16 is approximately 50 millimeters in length, the blood gas equilibrates within probe 10 in approximately 2 ½ minutes.

In addition, the volume of probe 10 should also be kept as small as reasonably possible. When probe 10 is introduced into the blood vessel, it purturbates the system because a small amount of volume has been added to the system, and blood gas required to equilibrate in that volume is removed from the system. However, once equilibration is reached, the present system introduces no more purturbations, unlike prior systems which purturbated the system each time a sensor reading was taken.

Figure 1A:
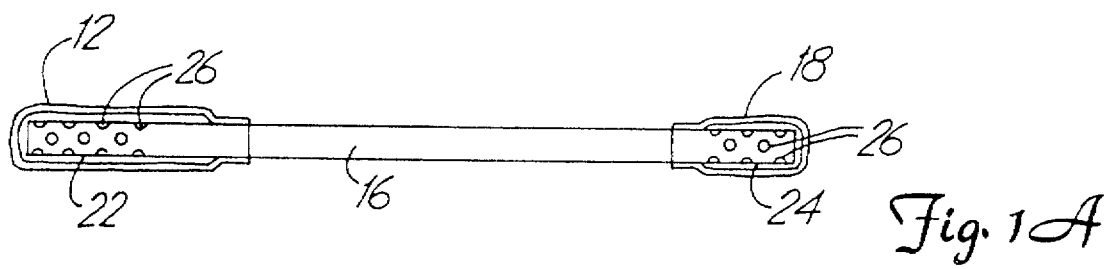
FIG. 1A is a side view of an alternative embodiment of the probe shown in FIG. 1.

In the preferred embodiment, support members 14 and 20 are coiled noble metal springs which support membranes 12 and 18, respectively. It is to be understood that support members 14 and 20 can be any suitable support members for supporting the membranes. FIG. 1A shows an alternative embodiment in which tube 16 is extended and discrete support members 14 and 20 are removed. In the embodiment shown in FIG. 1A, tube 16 has a first end 22 and a second end 24. Ends 22 and 24 are perforated, preferably using a laser, to have a number of apertures 26. Ends 22 and 24 support membranes 12 and 18, respectively. The apertures 26 allow the blood gases to diffuse across the membranes into the equilibration tubule of tube 16.

Probe 10 can be constructed in any number of suitable fashions. However, in one preferred embodiment, support members 14 and 20 are placed inside members 12 and 18. Then, membranes 12 and 18 are swollen or stretched. The ends of tube 16 are then placed within membranes 12 and 18, respectively. Membranes 12 and 18 are then allowed to retract to their original size thus shrinking onto the ends of tube 16. Membranes 12 and 18 can be swollen using a suitable gas or can be heat shrinkable materials which can be heat shrunk onto tube 16.

Figure 1B:
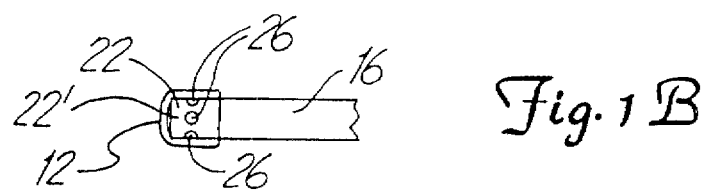
FIG. 1B is a side view of a portion of a second alternative embodiment of the probe shown in FIG. 1.

FIG. 1B is a second alternative embodiment of probe 10. In FIG. 1B, only end 22 of probe 10 is shown for the sake of clarity. However, it is to be understood that the arrangement shown in FIG. 1B can also be used in attaching membrane 18 to tube 16. FIG. 1B shows that only four apertures 26 (one of which is not shown) are drilled in end 22 of tube 16. In addition, the axial end 22' of tube 16 is open. Membrane 12 thus is formed over apertures 26, and over axial end 22' of tube 16.

Figure 1C:
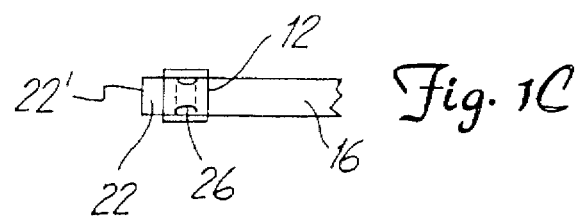
FIG. 1C is a side view of a portion of a third alternative embodiment of the probe shown in FIG. 2.

FIG. 1C shows a third embodiment of one feature of the present invention. As in FIG. 1B, apertures 26 are formed in end 22 of tube 16. However, in FIG. 1C, only two apertures 26 are formed in end 22. In addition, in FIG. 1C, axial end 22' of tube 16 is sealed so that membrane 12 need only be formed as a strip covering apertures 26.

One advantage of the present invention is that membrane 18 has an active surface area through which blood gases diffuse that is relatively large. Therefore, when membrane 12 is located in the bloodstream, if a blood clot forms on a portion of membrane 12, there is still likely to be a large portion of the active surface area of membrane 12 through which blood gas can diffuse. Thus, blood clots cannot easily destroy the functionality of probe 10. In addition, should end 22 of probe 10 engage the side of the blood vessel into which it is inserted, and be partially covered by plaque on the side of the vessel, end 22 is not likely to be entirely covered by the plaque. Therefore, there is likely to be a large portion of the active surface area of membrane 12 available for blood gas diffusion. To this end, it is preferred that end 22, when formed with apertures 26, have at least two apertures radially opposed to one another about the periphery of end 22. By having apertures 26 in radial opposition, the chances of having a blood clot cover both apertures 26 is very small. In addition, the likelihood that both apertures 26 would be covered by plaque on the side of the blood vessel is also very small.

The diameter of apertures 26 is presently contemplated to be 0.005 inches. Thus, the surface area of membrane 12 should be at least large enough to cover both apertures 26. The preferred minimum surface area for membrane 12 is approximately $3.925 \times 10^{-5}$ square inches. It should be noted that this surface area is significantly larger than the surface area of prior art sensors which were inserted directly into the bloodstream. With such prior art sensors, if a clot formed on the sensor, it substantially covered the entire sensing surface rendering the sensor useless. In addition, if the sensors were in engagement with plaque on the side of the blood vessel, they were also likely to be entirely covered, thereby rendered useless.

FIG. 2 is a side sectional view of blood gas probe 10 shown in FIG. 1 along with an oxygen sensor 25 and a carbon dioxide sensor 27 mounted proximate membrane 18. A sensor housing 28 defines an electrolyte chamber 30 which encompasses membrane 18. Sensor housing 28 includes a pair of sensor surfaces 32 and 34. Surfaces 32 and 34 are used to mount conventional $CO_2$ and $O_2$ sensors, 27 and 25, respectively. Once gas diffuses down tube 16 and into the interior chamber defined by membrane 18, it begins to diffuse across membrane 18 into electrolyte chamber 30. As indicated earlier, when probe 16 is approximately 50 millimeters in length, it takes approximately 2½ minutes for gas to diffuse through tube 16, across membrane 18, and equilibrate with other gases in the tube such that, the gases in electrolyte chamber 30 can be sensed by the $O_2$ and $CO_2$ sensors 25 and 27 to determine gas concentrations in the bloodstream. It should be noted that the $O_2$ and $CO_2$ sensors can be any suitable form of gas sensors which operate on electrochemical, optical, or other principles to sense the desired gases. Also, the sensors 25 and 27 can be disposable or reusable sensors, as desired. The electrolyte located in electrolyte chamber 30 is to be a suitable solution for use with the particular $O_2$ and $CO_2$ sensors 25 and 27 chosen. The electrolyte is commonly specified by the manufacturer of such sensors. It should also be noted that, while sensors 25 and 27 are shown in opposing relation, they could also be mounted axially relative to tube 16 or in a planar fashion relative to one another.

In the preferred embodiment, sensor housing 28 is provided with a shutter 35, or other closable aperture, and concentrically arranged tubes 71 and 73 coupled to housing 28 adjacent shutter 35. Shutter 35 and tubes 71 and 73 are provided as a means for calibrating the $O_2$ and $CO_2$ sensors 25 and 27 located on surfaces 32 and 34. To calibrate the sensors, shutter 35 is opened and electrolyte chamber 30 is flooded with flowing calibration gas (or zero gas) by tube 71. Circulation of the calibration gas is provided through return tube 73. By introducing a high pressure calibration gas flowing past electrolyte chamber 30, the arterial blood gases are swept out of electrolyte chamber 30 and replaced by the calibration gas. The calibration gas is preferably an inert gas such as argon.

Once the calibration gas has been introduced into electrolyte chamber 30 at sufficient pressure, sensor readings are taken to assure that sensors 25 and 27 are reading properly. If not, sensors 25 and 27 are calibrated for any maladjustment. Then, a span gas having a known concentration of $O_2$ and $CO_2$ is introduced through shutter 35. Readings are again taken by sensors 25 and 27 and necessary adjustments are made.

In one preferred embodiment, electrolyte chamber 30 is first flooded with argon to provide a zero or baseline reading for the sensors 25 and 27. Then, a high pressure span gas of 10% $CO_2$ and 90% $O_2$ is introduced into electrolyte chamber 30. Readings are taken from sensors 25 and 27 and proper calibration is undertaken. This process can either be done automatically or manually at given intervals or as desired by the physician. It should be noted that, whatever configuration shutter 35 takes, it should add as little dead space into the system as possible to enhance the equilibration time of the system.

FIG. 3 shows an ex vivo end of the blood gas probe 10 shown in FIGS. 1 and 2. Similar items are similarly numbered to those shown in FIGS. 1 and 2. FIG. 3 shows the ex vivo end of probe 10 with membrane 18 mounted within a sensor housing 28. In this preferred embodiment, probe 10 is, for instance, located within a standard 22 gauge cannula introducer 38. Introducer 38 has a flared end portion 42 with a threaded annular exterior surface 43 threadably coupled to a blood pressure line and sensor cable connector 49 by a standard Leur nut 44. Leur nut 44 has a tapered end 61 referred to as the Leur taper. Leur taper 61 extends within the flared end 42 of introducer 38. In the preferred embodiment, Leur taper 61 defines an opening 63 in which sensor housing 28 is located. Sensor housing 28 may be a part, separated from Leur nut 44 and fixed within opening 65 by welding, adhesive, or any suitable connection method. Alternatively, sensor housing 28 is formed integrally with Leur nut 44.

In the preferred embodiment, introducer 38 has an inner diameter which is slightly larger than the outer diameter of probe 10. Thus, as introducer 38 and probe 10 are introduced into the artery, there is a passage 39, between the exterior surface of probe 10 and the interior surface of introducer 38, which communicates with the ex vivo flared end 42 of introducer 38 and with the bloodstream under analysis. This passage 39 also communicates with an annular blood pressure passage 50 through Leur taper 61. Passage 50 in turn, mates with, and communicates with, standard blood pressure lines 51 and 53 which join and provide a singular blood pressure line outlet 55. Outlet 55 is coupled to an external blood pressure line 56 by a standard Leur nut 54.

Also, FIG. 3 shows that the carbon dioxide and oxygen sensors 25 and 27 are coupled to conductors 45 and 46, respectively. Conductors 45 and 46 extend through connector 49 and into sensor cable 48. Sensor cable 48 carries conductors 45 and 46 to a desired signal processing apparatus, such as a digital computer, within which the desired analysis is completed. It should also be noted that amplification or other desired signal conditioning can be provided either at the location of electrolyte chamber 28 or at any desirable point along conductors 45 and 46.

Figure 4:
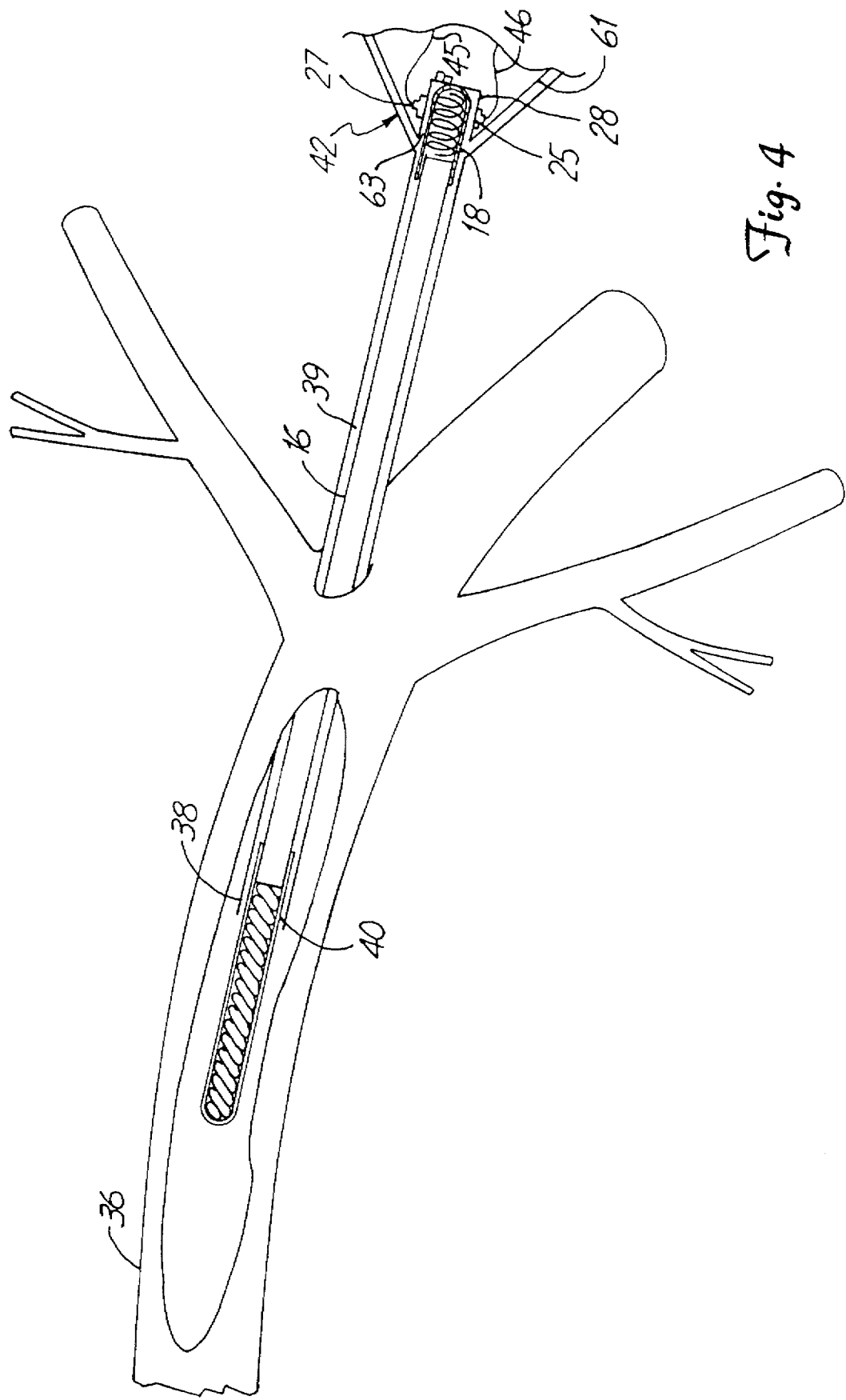
FIG. 4 illustrates the blood gas probe of FIG. 1 in use.

FIG. 4 shows blood gas probe 10 in use in an artery 36. Introducer 38 is used to introduce probe 10 into artery 36. Once probe 10 is introduced into artery 36 within introducer 38 probe 10 is extended from within introducer 38 so that membrane 12 is in contact with blood in artery 36. This allows arterial blood gas to be monitored to diffuse across membrane 12, down tube 16, into the interior of membrane 18, to fill electrolyte chamber 30 defined by housing 28 and to equilibrate. Once in equilibrium, the sensors 25 and 27 coupled to the ex vivo end of blood gas probe 10 sense the desired blood gases.

FIG. 4 also shows blood pressure communication channel 39 which directly communicates with blood pressure in artery 36 to allow the blood pressure to be measured at the ex vivo end of probe 10.

CONCLUSION

The present invention provides a blood gas probe 10, and a corresponding technique and system for measuring or monitoring arterial blood gas on a continuous basis without removing any significant sample from the system under analysis. While the present invention does remove some gas due to the electrochemical or other reaction at the sensors, such a trivial amount of consumption is insignificant in determining the measurements being taken. Further, the present invention provides a system in which the sensors are located external to the body. This provides efficiency in calibrating the sensors.

It should also be noted that, in certain circumstances, it may be desirable to have the sensors used with the present invention measure the blood gas in the gas phase. In such an embodiment, gas would preferably be sensed using Raman spectroscopy or another similar sensor technique, and there would be no need for electrolyte in chamber 30.

Further, the present sensors can be provided with their own gas permeable membrane. In such an embodiment, the electrolyte is contained within the sensor itself, and the electrolyte in chamber 30, as well as membrane 18, can be eliminated. Once the gases have diffused from the blood stream through probe 10, the gases then diffuse through the gas permeable membranes provided with each sensor and through the sensor electrolyte. Once this entire system is in equilibrium, readings are taken from the sensors 25 and 27 to determine gas levels of the desired gases.

Finally, it should be noted that the present invention can be used in monitoring other blood gases, besides carbon dioxide and oxygen. It is to be understood that, for purposes of the present description, the term blood gas includes anesthetic agent vapor dissolved in the blood. With the appropriate sensors in place, one can essentially measure any desired blood gas using the present invention.

Although the present invention has been described with reference to preferred embodiments, workers skilled in the art will recognize that changes may be made in form and detail without departing from the spirit and scope of the invention.

What is claimed is:

1. A blood gas monitoring system for monitoring blood gas from blood in a blood vessel, the system comprising:
   a probe having a probe chamber with a first end and a second end;
   a first gas permeable membrane coupled to the probe at the first end of the probe chamber;
   sensing means disposed at the second end of the probe chamber for sensing a desired characteristic of the blood gas;
   wherein, when the first gas permeable membrane is introduced into the blood vessel, blood gas diffuses through the first gas permeable membrane and throughout the probe chamber and substantially equilibrates with the blood gas in the blood vessel, the sensing means being disposed to sense the desired characteristic of the blood gas in the probe chamber which has substantially equilibrated with the blood gas in the blood vessel once the blood gas in the probe chamber reaches substantial equilibrium with the blood gas in the blood vessel, support means, coupled to the probe for supporting the first gas permeable membrane; and
   a second gas permeable membrane coupled to the second end of the probe.

2. The blood gas monitoring system of claim 1 wherein the support means comprises:
   a noble metal support member coupled to the probe and inserted within the first gas permeable membrane.

3. The blood gas monitoring system of claim 2 wherein the noble metal support member comprises:
   a noble metal coil.

4. The blood gas monitoring system of claim 1 and further comprising:
   second support means, coupled to the probe, for supporting the second gas permeable membrane.

5. The blood gas monitoring system of claim 4 wherein the second support means comprises:
   a noble metal support member coupled within the second gas permeable membrane.

6. The blood gas monitoring system of claim 4 wherein the second support means comprises:
   the second end of the probe, the second end of the probe extending within the second gas permeable membrane and including apertures to allow the blood gas to diffuse from the probe chamber across the second gas permeable membrane.

7. The blood gas monitoring system of claim 4 and further comprising:
   an electrolyte chamber, coupled about the second gas permeable membrane and being filled with an electrolyte, wherein the sensing means is disposed proximate the electrolyte chamber and relative to the second gas permeable membrane to sense blood gas which diffuses across the second gas permeable membrane and into the electrolyte chamber.

8. The blood gas monitoring system of claim 1 and further comprising:
   introducing means, housing the probe and the first gas permeable membrane, for introducing the probe and the first gas permeable membrane into the blood vessel.

9. The blood gas monitoring system of claim 8 wherein the introducing means comprises:
   a tube having an inner diameter larger than an outer diameter of the probe, the inner diameter of the tube and the outer diameter of the probe defining a passageway adapted to communicate with blood pressure in the blood vessel when the probe is introduced into the blood vessel, the passageway adapted to be coupled to a blood pressure outlet at an ex vivo end of the blood gas monitoring system.

10. The blood gas monitoring system of claim 9 wherein the introducing means comprises:
    a cannula introducer.

11. The blood gas monitoring system of claim 1 wherein the sensing means comprises:
    an oxygen sensor.

12. The blood gas monitoring system of claim 1 wherein the sensing means comprises:
    a carbon dioxide sensor.

13. A blood gas monitoring probe, comprising:
    a housing having a first end and a second end and defining a probe chamber;
    a first gas permeable membrane coupled to the first end of the housing;
    a second gas permeable membrane coupled to the second end of the housing;
    a sensor chamber, disposed about the second gas permeable membrane;
    sensing means, coupled to the sensor chamber, for sensing a desired gas characteristic; and
    wherein the first gas permeable membrane is inserted in a blood vessel and gas from blood in the blood vessel diffuses across the first gas permeable membrane throughout the probe chamber and the sensor chamber and reaches equilibrium with gas in the blood, the sensing means sensing the desired gas characteristic when the diffused gas reaches equilibrium with the gas in the blood.

14. A gas monitoring system for monitoring gas from a desired environment, the system comprising:
    a probe having a probe chamber with a first end and a second end;
    a first gas permeable membrane coupled to the probe at the first end of the probe chamber;
    sensing means disposed at the second end of the probe chamber for sensing a desired characteristic of the gas;
    wherein, when the first gas permeable membrane is introduced into the environment, gas diffuses through the first gas permeable membrane and throughout the probe chamber and substantially equilibrates with the gas in the environment, the sensing means being disposed to sense the desired characteristic of the gas in the probe chamber which has substantially equilibrated with the gas in the environment once the gas in the probe chamber reaches substantial equilibrium with the gas in the environment; and support means, coupled to the probe for supporting the first gas permeable membrane; and a second gas permeable membrane coupled to the second end of the probe.

15. The gas monitoring system of claim 14 wherein the support means comprises:

a noble metal support member coupled to the probe and inserted within the first gas permeable membrane.

16. The gas monitoring system of claim 15 wherein the noble metal support member comprises:

a noble metal coil.

17. The gas monitoring system of claim 14 wherein the support means comprises:

an end of the probe extending within the first gas permeable membrane, the end of the probe including apertures to allow the gas to diffuse across the first gas permeable membrane and into the probe chamber.

18. The gas monitoring system of claim 17 wherein the end of the probe includes two apertures radially opposing one another about a periphery of the end of the probe.

19. The gas monitoring system of claim 14 and further comprising:

second support means, coupled to the probe, for supporting the second gas permeable membrane.

20. The gas monitoring system of claim 19 wherein the second support means comprises:

a noble metal support member coupled within the second gas permeable membrane.

21. The gas monitoring system of claim 19 wherein the second support means comprises:

the second end of the probe, the second end of the probe extending within the second gas permeable membrane and including apertures to allow the gas to diffuse from the probe chamber across the second gas permeable membrane.

22. The blood gas monitoring system of claim 14 and further comprising:

introducing means, housing the probe and the first gas permeable membrane, for introducing the probe and the first gas permeable membrane into the environment.

23. A blood gas monitoring system for monitoring blood gas from blood in a blood vessel, the system comprising:

a probe having a probe chamber with a first end and a second end;

a first gas permeable membrane coupled to the probe at the first end of the probe chamber;

sensing means disposed at the second end of the probe chamber for sensing a desired characteristic of the blood gas;

wherein, when the first gas permeable membrane is introduced into the blood vessel, blood gas diffuses through the first gas permeable membrane and throughout the probe chamber and substantially equilibrates with the blood gas in the blood vessel, the sensing means being disposed to sense the desired characteristic of the blood gas in the probe chamber which has substantially equilibrated with the blood gas in the blood vessel once the blood gas in the probe chamber reaches substantial equilibrium with the blood gas in the blood vessel; and an end of the probe extending within the first gas permeable membrane, the end of the probe including apertures to allow the blood gas to diffuse across the first gas permeable membrane and into the probe chamber, wherein the end of the probe includes two apertures radially opposing one another about a periphery of the end of the probe.

24. A blood gas monitoring system for monitoring blood gas from blood in a blood vessel, the system comprising:

a probe having a probe chamber with a first end and a second end;

a first gas permeable membrane coupled to the probe at the first end of the probe chamber;

sensing means disposed at the second end of the probe chamber for sensing a desired characteristic of the blood gas;

wherein, when the first gas permeable membrane is introduced into the blood vessel, blood gas diffuses through the first gas permeable membrane and throughout the probe chamber and substantially equilibrates with the blood gas in the blood vessel, the sensing means being disposed to sense the desired characteristic of the blood gas in the probe chamber which has substantially equilibrated with the blood gas in the blood vessel once the blood gas in the probe chamber reaches substantial equilibrium with the blood gas in the blood vessel;

wherein the sensing means includes a sensing element with a sensing surface area for sensing the desired characteristic, and wherein the first gas permeable membrane has a surface area through which the blood gas diffuses that is large relative to the sensing surface area of the sensing element.

25. A gas monitoring system for monitoring gas from a desired environment, the system comprising:

a probe having a probe chamber with a first end and a second end;

a first gas permeable membrane coupled to the probe at the first end of the probe chamber;

sensing means disposed at the second end of the probe chamber for sensing a desired characteristic of the gas;

wherein, when the first gas permeable membrane is introduced into the environment, gas diffuses through the first gas permeable membrane and throughout the probe chamber and substantially equilibrates with the gas in the environment, the sensing means being disposed to sense the desired characteristic of the gas in the probe chamber which has substantially equilibrated with the gas in the environment once the gas in the probe chamber reaches substantial equilibrium with the gas in the environment;

an end of the probe extending within the first gas permeable membrane, the end of the probe including apertures to allow the gas to diffuse across the first gas permeable membrane and into the probe chamber; and wherein the end of the probe includes two apertures radially opposing one another about a periphery of the end of the probe.

* * * * *